(12) United States Patent
Miyajima et al.

(10) Patent No.: US 9,459,162 B2
(45) Date of Patent: Oct. 4, 2016

(54) DEVICE FOR MEASURING MECHANICAL QUANTITY

(75) Inventors: Kentaro Miyajima, Tokyo (JP); Kisho Ashida, Tokyo (JP); Hiroyuki Oota, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 144 days.

(21) Appl. No.: 14/379,683

(22) PCT Filed: Mar. 2, 2012

(86) PCT No.: PCT/JP2012/055447
§ 371 (c)(1),
(2), (4) Date: Aug. 19, 2014

(87) PCT Pub. No.: WO2013/128643
PCT Pub. Date: Sep. 6, 2013

(65) Prior Publication Data
US 2015/0020601 A1    Jan. 22, 2015

(51) Int. Cl.
*G01L 1/22* (2006.01)
*G01B 7/16* (2006.01)
*G01L 1/04* (2006.01)
(Continued)

(52) U.S. Cl.
CPC ............... *G01L 1/2293* (2013.01); *G01B 7/16* (2013.01); *G01B 7/18* (2013.01); *G01L 1/044* (2013.01); *G01L 1/18* (2013.01); *G01L 1/2262* (2013.01); *G01L 1/2281* (2013.01); *G01N 19/00* (2013.01)

(58) Field of Classification Search
CPC .................................. G01L 1/22; G01B 7/16
USPC ........................................................ 73/777
See application file for complete search history.

(56) References Cited

U.S. PATENT DOCUMENTS

| 7,484,422 B2* | 2/2009 | Sumigawa | ............... G01B 7/18 73/760 |
| 7,518,202 B2* | 4/2009 | Tanie | ........................ G01B 7/18 257/417 |

(Continued)

FOREIGN PATENT DOCUMENTS

JP        7-36010 U      7/1995
JP       10-227607 A     8/1998

(Continued)

OTHER PUBLICATIONS

International Search Report dated Apr. 10, 2012 with English translation (five (5) pages).

*Primary Examiner* — Lisa Caputo
*Assistant Examiner* — Octavia Hollington
(74) *Attorney, Agent, or Firm* — Crowell & Moring LLP

(57) ABSTRACT

A device for measuring mechanical quantity is provided which reduces the influence of a difference in thermal expansion coefficient between an object to be measured and a base plate metal body, and precisely measures a mechanical quantity such as deformation quantity or strain quantity caused in the object to be measured. The device includes a semiconductor strain sensor module for measuring deformation quantity of the object to be measured, and the module includes a metal body, and a semiconductor strain sensor mounted on the metal body to detect strain of the metal body. The object to be measured is made of a material having a thermal expansion coefficient larger than that of the metal body. Further, the metal body mounted with the semiconductor strain sensor has a structure configured to be fixed to the object to be measured.

7 Claims, 17 Drawing Sheets

(51) Int. Cl.
*G01L 1/18* (2006.01)
*G01N 19/00* (2006.01)

(56) References Cited

U.S. PATENT DOCUMENTS

| | | | |
|---|---|---|---|
| 8,438,931 B2 * | 5/2013 | Kazama | G01B 7/16 257/417 |
| 2006/0207339 A1 | 9/2006 | Sumigawa et al. | |
| 2007/0240519 A1 | 10/2007 | Shimazu et al. | |
| 2009/0199650 A1 | 8/2009 | Shimazu et al. | |

FOREIGN PATENT DOCUMENTS

| | | |
|---|---|---|
| JP | 2006-258674 A | 9/2006 |
| JP | 2007-10444 A | 1/2007 |
| JP | 2007-255953 A | 10/2007 |
| JP | 2009-264976 A | 11/2009 |

* cited by examiner (a)

(b)

(a)

(b)

(a)

(b)

(a)

(b)

(a)

(b)

(a)

(b)

(a)

(b)

(a)

(b)

(a)

(b)

DEVICE FOR MEASURING MECHANICAL QUANTITY

TECHNICAL FIELD

The present invention relates to a device for measuring mechanical quantity, and particularly to a device for measuring mechanical quantity generated in an object to be measured having a large thermal expansion coefficient such as a resin.

BACKGROUND ART

For example, as a technique relating to a device for measuring mechanical quantity, a strain gauge is often used in order to measure the strain or stress of a structure. The strain gauge has a structure in which a wiring pattern on a metal thin film of Cu—Ni alloy or Ni—Cr alloy is covered with a polyimide or epoxy resin film. The strain gauge is used by being bonded to the object to be measured with an adhesive. The strain gauge can calculate a strain quantity based on the resistance change of the metal thin film being strained and deformed.

Further, a semiconductor strain sensor is employed which has a strain detection unit using not the metal thin film but semiconductor piezoresistance formed by doping impurities in a semiconductor such as silicon. The semiconductor strain sensor has a resistance change rate relative to strain, which resistance change is several ten times as large as that of the strain gauge using the metal thin film, and the semiconductor strain sensor is allowed to measure minute strain. The strain gauge having the metal thin film has a small resistance change, so that an obtained electric signal needs to be amplified, and thus another external amplifier is required. The semiconductor strain sensor has a large resistance change, on the other hand, so that an obtained electric signal can be used without an external amplifier, and the semiconductor strain sensor may include a semiconductor strain gauge chip in which an amplifier circuit is integrated. Therefore, the application or convenience in use of the strain sensor is expected to significantly increase.

The semiconductor strain sensor has a semiconductor strain sensor chip obtained by chipping a silicon wafer on which impurities have been doped or wiring has been formed by a conventional semiconductor production technique. The chip (hereinafter referred to as semiconductor strain sensor chip) is incorporated into a device including a plastic resin or the like to measure a mechanical quantity such as manual or mechanical deformation quantity or stress input to a housing. In order to obtain electrical output according to the input in the measurement, it is important to accurately transmit, to the semiconductor strain sensor chip, the deformation quantity or strain quantity of the housing as an object to be measured, and it is also important to modularize the semiconductor strain sensor chip as well as to mount the semiconductor strain sensor to the object to be measured.

A technique relating to such a semiconductor strain sensor chip includes, for example, a technique described in PTL 1. PTL 1 discloses a method for joining a semiconductor strain sensor chip to a base plate and connecting the base plate to an object to be measured through two connection areas on the base plate on both sides of the semiconductor strain sensor chip.

CITATION LIST

Patent Literature

PTL 1: JP 2009-264976 A

SUMMARY OF INVENTION

Technical Problem

Prior to the filing of the present application, the inventors of the present application have studied a method for incorporating a semiconductor strain sensor chip into an input device or the like made of a material, such as a plastic resin, having a thermal expansion coefficient larger than that of a metal, and measuring a mechanical quantity such as the deformation quantity or strain quantity of the plastic resin.

In the study, when the object to be measured has a thermal expansion coefficient larger than that of a base plate metal body by approximately one digit, as in the plastic resin, a method is employed for connecting the base plate to the object to be measured through two connection areas on both sides of the semiconductor strain sensor chip, as disclosed in PTL 1.

As a result of the study, the inventors of the present application found that when the object to be measured such as a plastic resin has a thermal expansion coefficient larger than that of the base plate metal body by approximately one digit, two fastened portions on both sides of the semiconductor strain sensor chip are drawn laterally by thermal expansion of the object to be measured, the base plate loses isotropy in expansion, influence of thermal strain is generated, and precision in measurement of the strain quantity is deteriorated.

The present invention has been made in view of such a study result, and it is a typical object of the present invention to provide a device for measuring mechanical quantity which can reduce the influence of a difference in thermal expansion coefficient between the object to be measured and the base plate metal body, and precisely measure the mechanical quantity such as deformation quantity or strain quantity generated in the object to be measured.

The above-mentioned and other objects and novel features of the present invention will be apparent from the description of the specification and the accompanying drawings.

Solution to Problem

The following is a brief description of the representative summary of the present invention disclosed in the present application.

A representative device for measuring mechanical quantity measures deformation quantity of an object to be measured, and the device has the following features. The device for measuring mechanical quantity includes a metal body, and a semiconductor strain sensor mounted on the metal body to detect the strain of the metal body. The object to be measured is made of a material having a thermal expansion coefficient larger than that of the metal body. Further, the metal body mounted with the semiconductor strain sensor has a structure configured to be fixed to the object to be measured. Especially, only one side of the metal body, on which the semiconductor strain sensor is mounted, is fixed to the object to be measured. Accordingly, the deformation quantity of the object to be measured can be detected using the semiconductor strain sensor on the metal body.

Another representative device for measuring mechanical quantity measures the deformation quantity of the object to be measured, and has the following features. The device for measuring mechanical quantity includes a metal body, a first semiconductor strain sensor, and a second semiconductor strain sensor. The metal body has a pipe shape. The first semiconductor strain sensor is mounted on the upper surface of the metal body to detect the strain of the metal body. The second semiconductor strain sensor is mounted on a side surface of the metal body to detect the strain of the metal body. The object to be measured is made of a material having a thermal expansion coefficient larger than that of the metal body. Still further, the metal body mounted with the first semiconductor strain sensor and the second semiconductor strain sensor has a structure to be fixed to the object to be measured. Especially, only one side of the metal body mounted with the first and second semiconductor strain sensors is fixed to the object to be measured. Accordingly, the deformation quantity of the object to be measured can be detected using the first semiconductor strain sensor and the second semiconductor strain sensor on the metal body.

Advantageous Effects of Invention

The following is a brief description of an effect obtained by a representative embodiment of the invention disclosed in the present application.

That is, by the representative effect, there can be provided a device for measuring mechanical quantity capable of reducing an influence of a difference in thermal expansion coefficient between the object to be measure and the base plate metal body and of precisely measuring mechanical quantity, such as deformation quantity or strain quantity, caused in the object to be measured.

DESCRIPTION OF EMBODIMENTS

Figure 1:
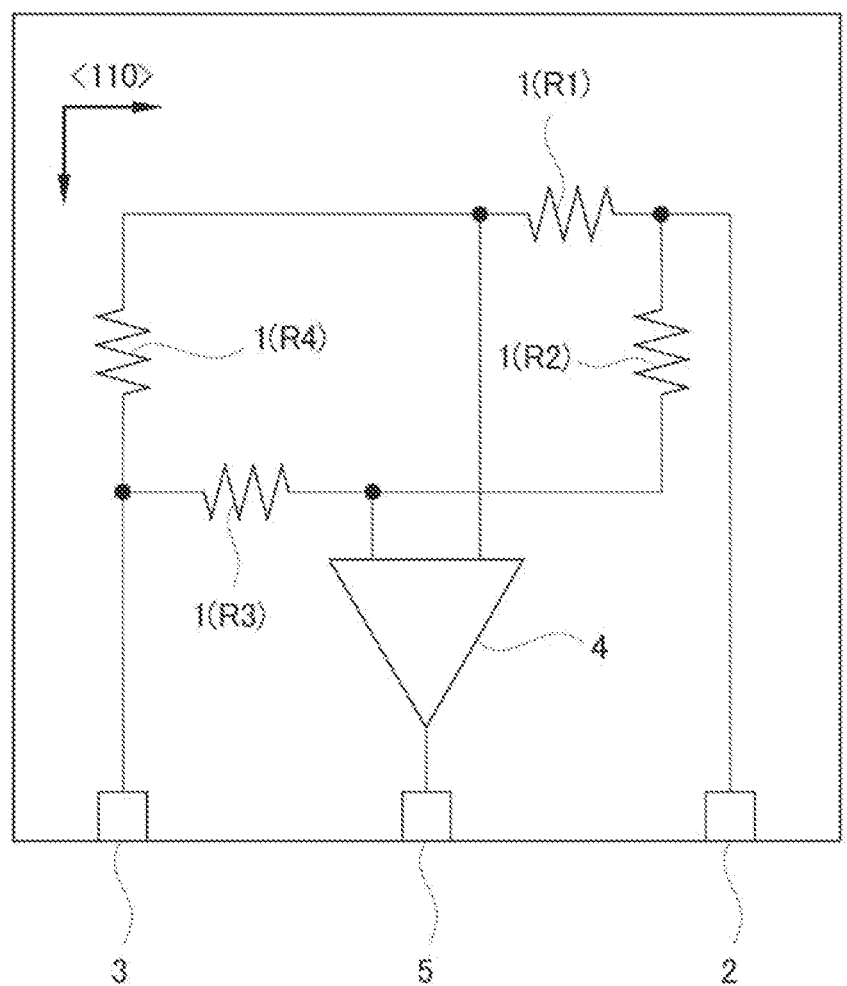
FIG. 1 shows an example of the principle (circuit) of a semiconductor strain sensor in a semiconductor strain sensor module as a first embodiment of a device for measuring mechanical quantity of the present invention.
Figure 2:
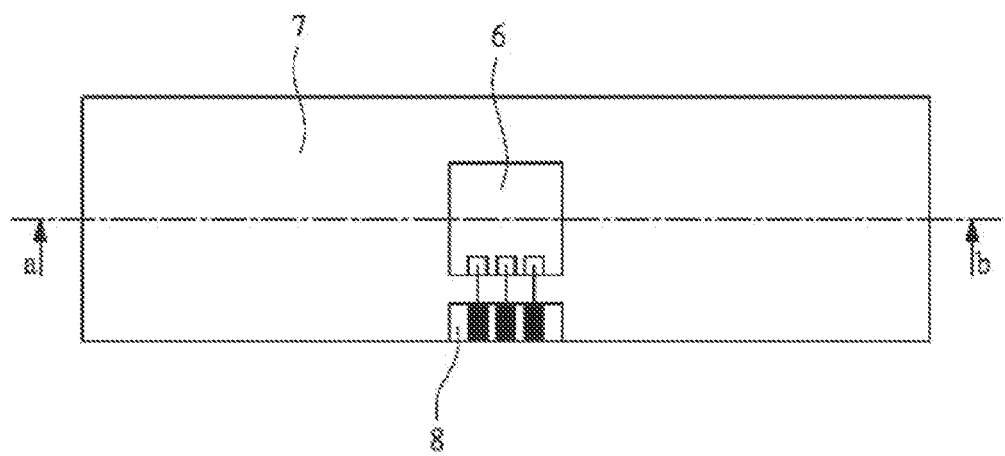
FIGS. 2(a) and 2(b) are a plan view and a cross-sectional view, respectively, showing an example of a structure of the semiconductor strain sensor module as the first embodiment of the device for measuring mechanical quantity of the present invention.
Figure 2:
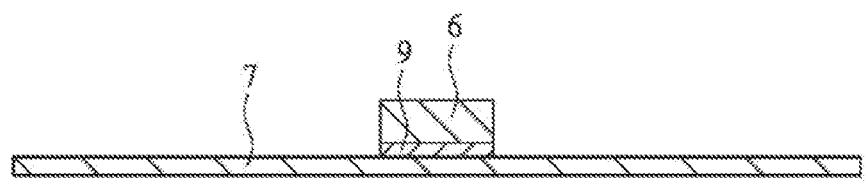
Figure 3:
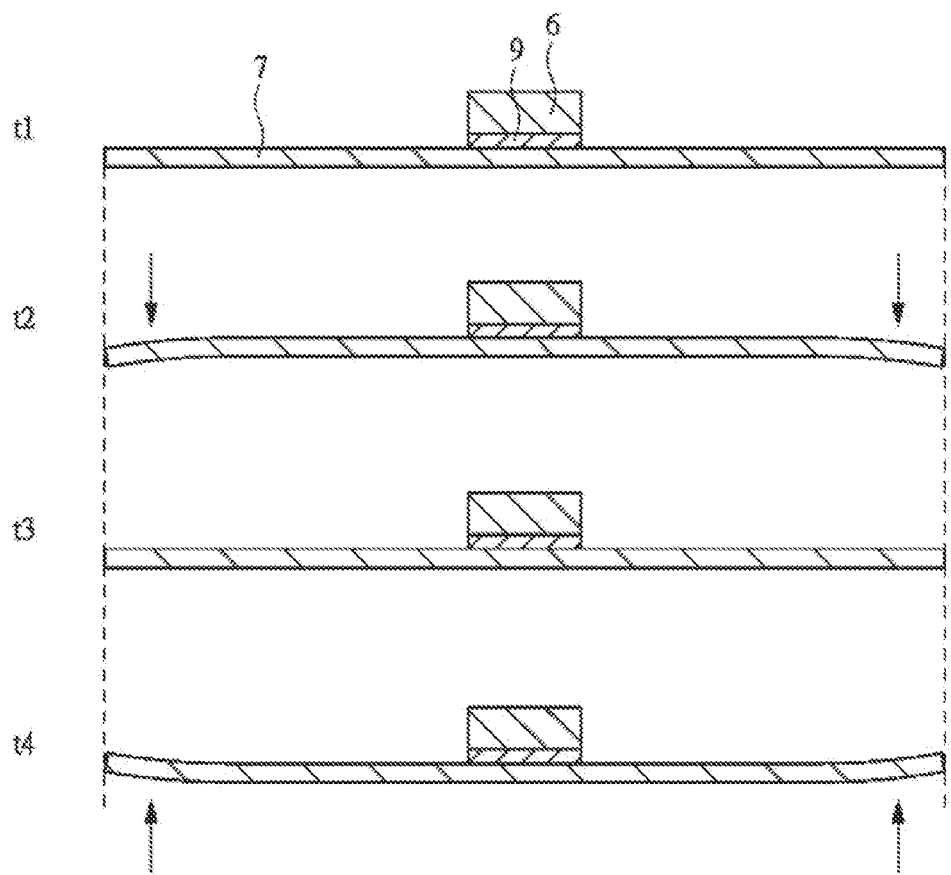
FIGS. 3(a) and 3(b) show an example of operations of a metal body having a semiconductor strain sensor and output voltages of the semiconductor strain sensor, in the semiconductor strain sensor module shown in FIGS. 2(a) and 2(b).
Figure 3:
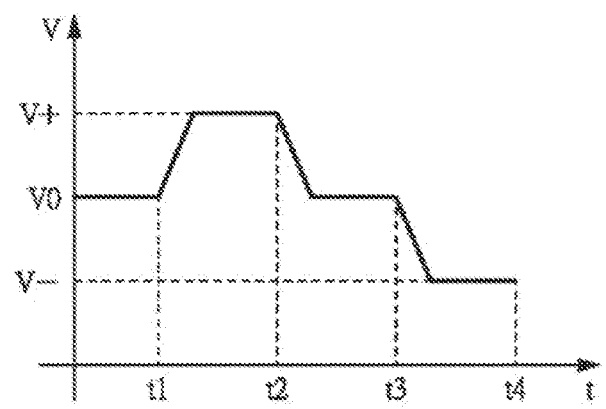

In the following embodiments, it should be noted that an explanation will be made in a plurality of embodiments or sections divided conveniently if desired, but the embodiments or sections are not irrelevant to each other unless otherwise stated and have a relationship between them in which one is a modification, detail, supplement, or the like of part or whole of another. Further, in the following embodiments, it should be noted that the number of elements or the like (including the number of elements, a value, a quantity, a range, or the like) which is made reference to is not limited to a specific number and may be equal to, or larger or smaller than the specific number unless otherwise stated or unless the number is obviously limited to the specific number in principle.

Still further, in the following embodiments, it goes without saying that the components (including element steps or the like) are not always essential unless otherwise stated or unless the components are considered to be obviously essential in principle. Similarly, in the following embodiments, it should be noted that the shape, positional relationship, or the like of the components which is made reference to substantially includes an approximate or similar one unless otherwise stated or unless otherwise considered in principle. The same is applied to the value and the range.

<Overview of Embodiments>

A device for measuring mechanical quantity (for example, corresponding components, reference signs, or the like are provided in parenthesis) according to an embodiment of the present invention is a device for measuring mechanical quantity (semiconductor strain sensor module) which is configured to measure a deformation quantity of an object (10) to be measured and has the following features. The device for measuring mechanical quantity includes a metal body (7) and a semiconductor strain sensor (6) mounted on the metal body to detect the strain of the metal body. The object to be measured is made of a material having a thermal expansion coefficient larger than that of the metal body. Further, the metal body mounted with the semiconductor strain sensor has a structure configured to be fixed to the object to be measured. Especially, only one side of the metal body, on which the semiconductor strain sensor is mounted, is fixed to the object to be measured. Accordingly, the deformation quantity of the object to be measured can be detected using the semiconductor strain sensor on the metal body.

The device for measuring mechanical quantity (for example, corresponding components, reference signs, or the like are provided in parenthesis) according to an embodiment of the present invention is a device for measuring mechanical quantity (semiconductor strain sensor module) which is configured to measure a deformation quantity of an object (23) to be measured and has the following features. The device for measuring mechanical quantity includes a metal body (20), a first semiconductor strain sensor (21), and a second semiconductor strain sensor (22). The metal body has a pipe shape. The first semiconductor strain sensor is mounted on the upper surface of the metal body to detect the strain of the metal body. The second semiconductor strain sensor is mounted on a side surface of the metal body to detect the strain of the metal body. The object to be measured is made of a material having a thermal expansion coefficient larger than that of the metal body. Still further, the metal body mounted with the first semiconductor strain sensor and the second semiconductor strain sensor has a structure to be fixed to the object to be measured. Especially, only one side of the metal body mounted with the first and second semiconductor strain sensors is fixed to the object to be measured. Accordingly, the deformation quantity of the object to be measured can be detected using the first semiconductor strain sensor and the second semiconductor strain sensor on the metal body.

The embodiments according to Overview of embodiments will be described in detail below based on the drawings. In all the drawings for showing the embodiments, the same member has the same reference sign in principle, and the repeated description thereof is omitted.

[First Embodiment]

A semiconductor strain sensor module as a first embodiment of a device for measuring mechanical quantity of the present invention will be described in detail using FIGS. 1 to 10.

<Semiconductor Strain Sensor Module>

The semiconductor strain sensor module according to the present embodiment will be described using FIGS. 1 to 4. In the semiconductor strain sensor module, the principle of a semiconductor strain sensor will be described first using FIG. 1. FIG. 1 shows an example of the principle (circuit) of the semiconductor strain sensor.

As shown in FIG. 1, the semiconductor strain sensor includes a bridge circuit obtained by combining a plurality of p-type diffused resistors 1 (R1, R2, R3, R4) disposed in such a manner that a silicon <110> orientation and a direction perpendicular to the silicon <110> orientation are positioned in current directions. As shown in FIG. 1, the p-type diffused resistors R1 and R3 have a current direction being the silicon <110> orientation, and the p-type diffused resistors R2 and R4 have a current direction perpendicular to the silicon <110> orientation.

The bridge circuit is connected to a power terminal 2 of a power potential and a ground terminal 3 of the ground potential, and output from the bridge circuit is amplified by an amplifier 4 incorporated into a semiconductor. That is, a connection point between the p-type diffused resistors R1 and R2 is connected to the power terminal 2, and a connection point between the p-type diffused resistors R3 and R4 is connected to the ground terminal 3. Further, a connection point between the p-type diffused resistors R4 and R1 is connected to one of input terminals of the amplifier 4, and a connection point between the p-type diffused resistors R2 and R3 is connected to the other input terminal of the amplifier 4. An output terminal of the amplifier 4 is connected to an output terminal 5 of the semiconductor strain sensor.

In the semiconductor strain sensor, when strain is generated in the silicon <110> orientation and a direction perpendicular to the silicon <110> orientation, resistance values of the p-type diffused resistors 1 (R1, R2, R3, R4) are changed, and the bridge circuit generates an output potential difference. The potential difference is amplified in the amplifier 4 incorporated in the semiconductor to obtain an electric signal according to a strain quantity from the output terminal 5.

In such a way, the semiconductor strain sensor includes the amplifier 4, the power terminal 2, the ground terminal 3, the output terminal 5, and the bridge circuit obtained by combining the p-type diffused resistors 1. The semiconductor strain sensor has a semiconductor strain sensor chip obtained by chipping a silicon wafer on which impurities have been doped or wiring has been formed by a semiconductor production technique.

Next, a structure of the semiconductor strain sensor module will be described using FIGS. 2(a) and 2(b). FIGS. 2(a) and 2(b) are a plan view and a cross-sectional view showing an example of a structure of the semiconductor strain sensor module (wherein the semiconductor strain sensor is connected to the metal body). FIG. 2(a) is a plan view, and FIG. 2(b) is a cross-sectional view taken along a cut line a-b shown in FIG. 2(a).

As shown in FIGS. 2(a) and 2(b), the semiconductor strain sensor module is configured such that the semiconductor strain sensor 6 (FIG. 1) is connected at substantially the center of the metal body 7 with a connection material 9 (e.g. metal solder or adhesive), and the terminals (power terminal 2, ground terminal 3, output terminal 5) of the semiconductor strain sensor 6 are connected to a terminal base 8 formed on the metal body 7, with a metal wire (e.g. gold wire). In FIGS. 2(a) and 2(b), the metal body 7 is formed into a plate shape, and has a rectangular shape elongated in the silicon <110> orientation of the semiconductor strain sensor 6.

In the structure of the semiconductor strain sensor module in which the semiconductor strain sensor 6 is connected to the metal body 7, an output voltage of the semiconductor strain sensor 6 which is generated upon generation of "bending strain" and "compression strain" on a surface of the metal body 7 having been applied with a longitudinal force, will be described using FIGS. 3(a) and 3(b). FIG. 3(a) shows an example of operations of the metal body 7 having the semiconductor strain sensor 6 and FIG. 3(b) shows output voltages of the semiconductor strain sensor 6. In FIGS. 3(a) and 3(b), t denotes a time and V denotes an output voltage of the semiconductor strain sensor 6.

A time t1 represents an initial condition at which any force is not applied to the metal body 7 and the output voltage of the semiconductor strain sensor 6 is V0. When a certain downward load is applied to both ends of the metal body 7 from the time t1 to a time t2, the "bending strain" is generated on the surface of the metal body 7, and the output voltage of the semiconductor strain sensor 6 rises up to an output voltage V+ through a transient condition. After that, the output voltage is returned to an initial condition from the time t2 and a time t3, and when a certain upward load is applied to the both ends of the metal body 7 from the time t3 to a time t4, the output voltage of the semiconductor strain sensor 6 falls to an output voltage V− through a transient condition. That is, the principle is used to estimate the strain generated in the metal body 7 and the load applied to the metal body 7 based on the output voltage of the semiconductor strain sensor 6.

Figure 4:
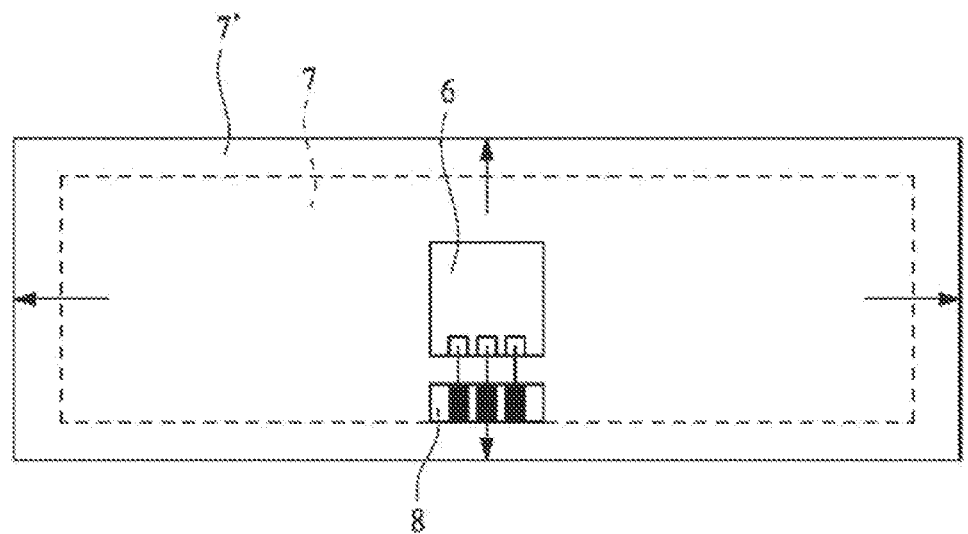
FIG. 4 shows an example of thermal expansion of the metal body having the semiconductor strain sensor in the semiconductor strain sensor module shown in FIGS. 2(a) and 2(b).

Further, the features of the semiconductor strain sensor module will be described using FIG. 4 representing a condition upon generation of the thermal expansion with the rise in temperature. FIG. 4 shows an example of thermal expansion of the metal body 7 having the semiconductor strain sensor 6.

In the semiconductor strain sensor module, when the temperature rises, the metal body 7 is isotropically expanded into a size of a metal body 7' (in FIG. 4, upward, rightward, downward, leftward, or the like in directions represented by arrows about a substantially center position of the metal body 7 on which the semiconductor strain sensor 6 is connected). In the output voltage of the semiconductor strain sensor 6, strain is canceled which is generated relative to the isotropic expansion by the structure of the bridge circuit in the semiconductor strain sensor 6, and the output voltage has a substantially constant value.

Measurement of the mechanical quantity of the object to be measured having a large thermal expansion coefficient, such as a plastic resin material, using the semiconductor strain sensor module described above, will be described below in detail.

<Structure Having Semiconductor Strain Sensor Module Fastened to Object to be Measured>

Figure 5:
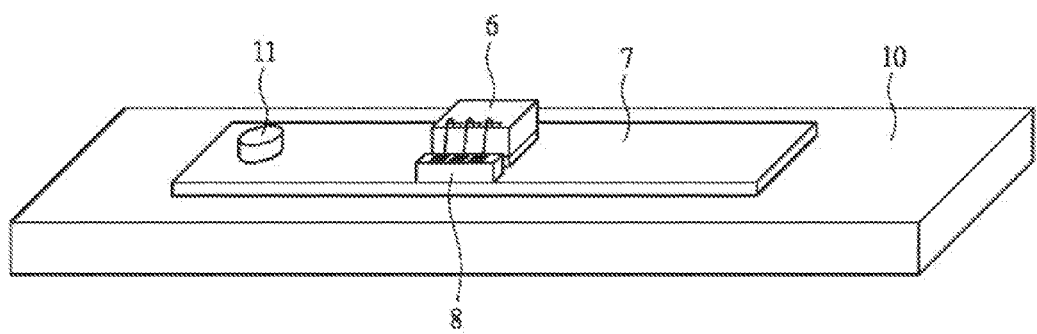
FIG. 5 is a perspective view showing an example of a structure in which the semiconductor strain sensor module shown in FIGS. 2(a) and 2(b) is fastened to an object to be measured.

A structure in which the above-mentioned semiconductor strain sensor module is fastened to the object to be measured will be described using FIGS. 5 to 7(b). First, the structure in which the semiconductor strain sensor module is fastened to the object to be measured will be described using FIGS. 5 to 6(b). FIG. 5 is a perspective view showing an example of the structure. FIG. 6(a) is a plan view and FIG. 6(b) is a cross-sectional view (cross-sectional view taken along a cut line a-b of FIG. 6(a)) which show an example of the structure.

Figure 6:
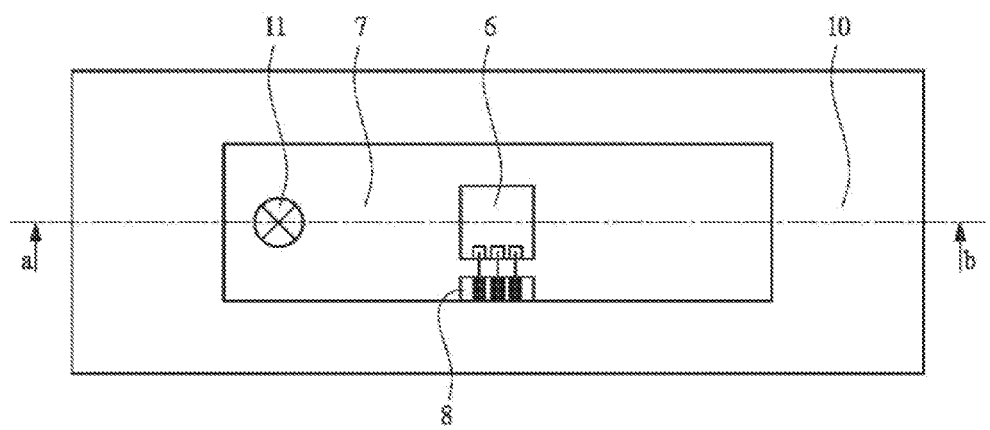
FIGS. 6(a) and 6(b) are a plan view and a cross-sectional view, respectively, showing an example of a structure in which the semiconductor strain sensor module shown in FIG. 5 is fastened to the object to be measured.
Figure 6:
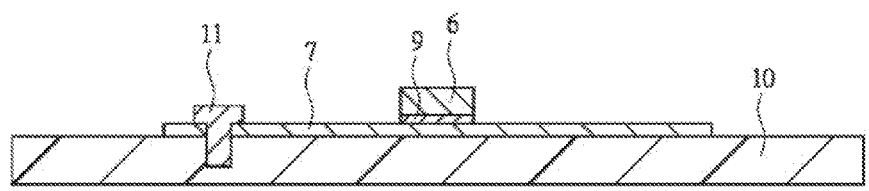
Figure 7:
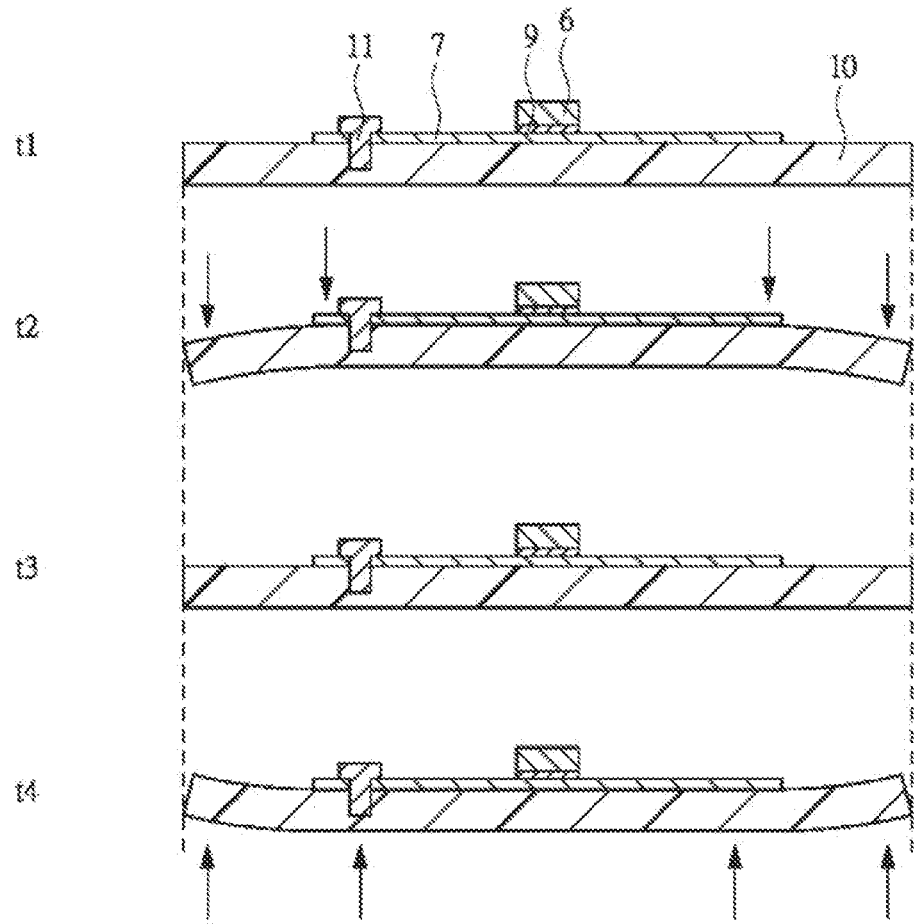
FIGS. 7(a) and 7(b) show an example of operations of the structure shown in FIGS. 6(a) and 6(b) in which the semiconductor strain sensor module is fastened to the object to be measured and output voltages of the semiconductor strain sensor.
Figure 7:
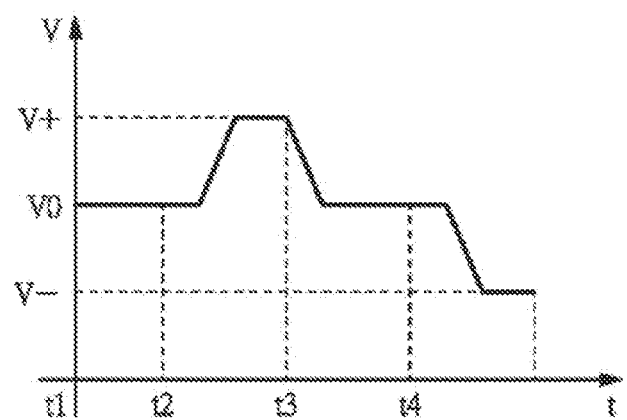

As shown in FIGS. 5 to 6(b), the structure is employed in which only one side of the semiconductor strain sensor module is fixed to the object 10 to be measured with a screw 11. In FIGS. 5 to 6(b), the semiconductor strain sensor 6 is connected to the metal body 7, the metal body 7 has two left and right portions on both longitudinal sides of the semiconductor strain sensor 6, the left side portion is connected to the object 10 to be measured with the screw 11 and the right side portion is not fixed to the object. A method for fixing the semiconductor strain sensor module on the object 10 to be measured may also employ welding by heat or adhesion with an adhesive in addition to the fastening with the screw 11. In any fixing method, it is important to fix only one side of the semiconductor strain sensor module.

Next, in the structure in which the semiconductor strain sensor module is fastened to the object 10 to be measured, as shown in FIGS. 5 to 6(b), operations of the semiconductor strain sensor 6 on the metal body 7 upon application of a load on the object 10 to be measured, will be described using FIGS. 7(a) and 7(b). FIG. 7(a) shows an example of operations of a structure in which the semiconductor strain sensor module is fastened to the object 10 to be measured, and FIG. 7(b) shows output voltages of the semiconductor strain sensor 6.

A time t1 represents an initial condition in which a force is not applied to the object 10 to be measured, wherein the output voltage of the semiconductor strain sensor 6 is denoted as V0. Then, when a certain downward load is applied to both ends of the object 10 to be measured from a time t2 to deform the object, a downward load proportional to the load on the object 10 to be measured is further applied to the metal body 7 connected to the object 10 to be measured with the screw 11, heat welding, adhesive or the like, "bending strain" is generated on a surface of the metal body 7, and the output voltage of the semiconductor strain sensor 6 rises to an output voltage V+ through a delay time from the initial condition to application of the strain to the metal body 7 and through a transient state.

Further, when the object 10 to be measured is restored to the initial condition from a time t3 and is applied with a certain upward load at both ends to be deformed from a time t4, the output voltage of the semiconductor strain sensor 6 falls to an output voltage V− through the delay time from the initial condition to the application of the strain to the metal body 7 and through the transient time. Accordingly, the principle allows the estimation of the deformation quantity or strain quantity of the object 10 to be measured based on the output voltage of the semiconductor strain sensor 6.

<Effect of First Embodiment>

Figure 8:
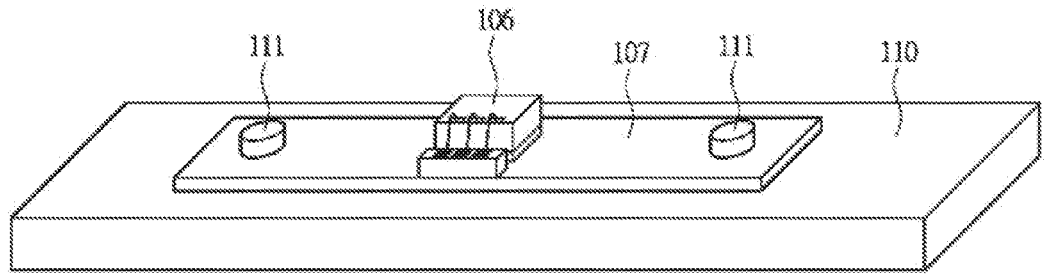
FIG. 8 is a perspective view showing a structure in which the semiconductor strain sensor module described in PTL 1 is fastened to the object to be measured.
Figure 9:
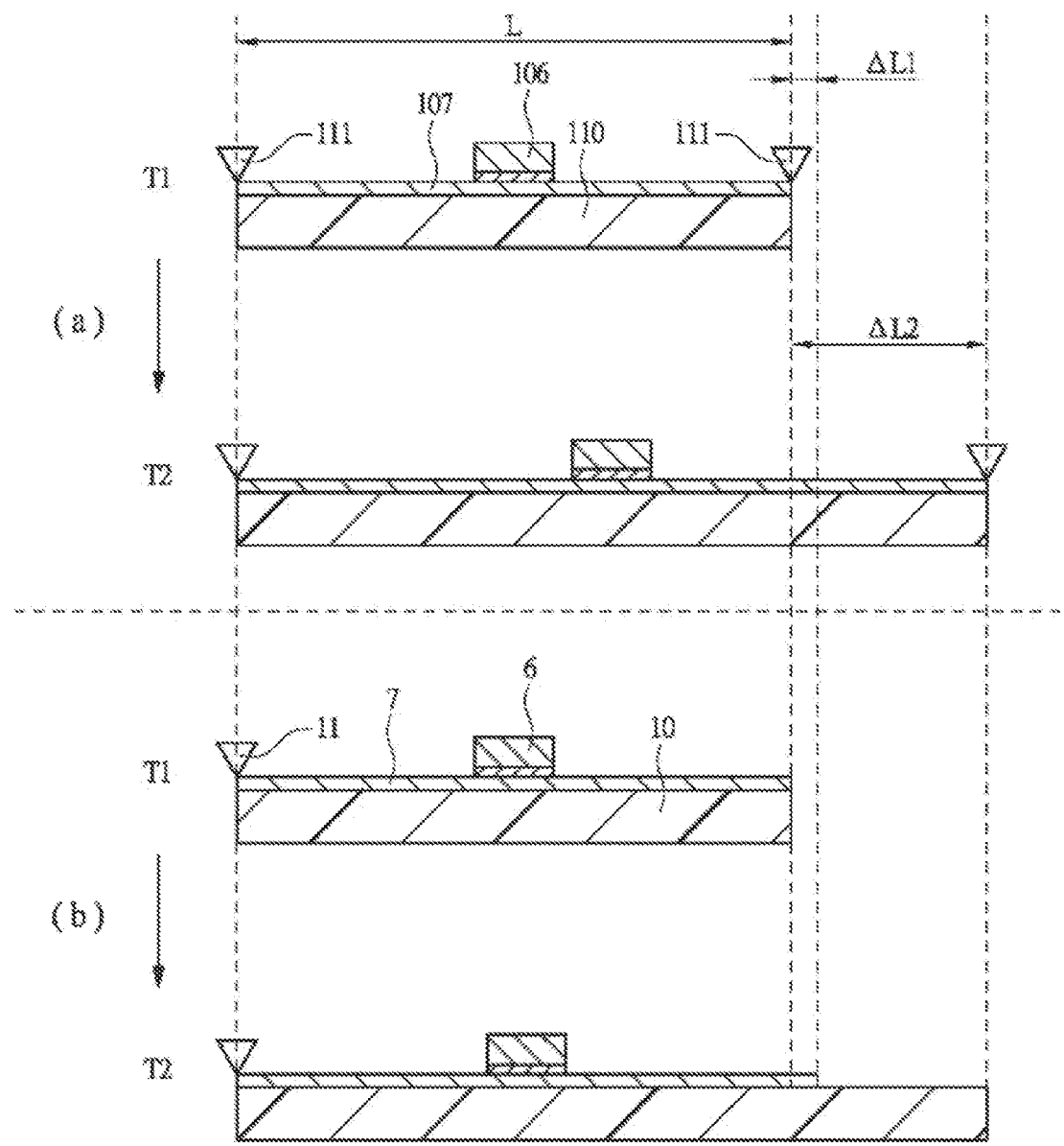
FIGS. 9(a) and 9(b) show an example of an effect of the semiconductor strain sensor module of the first embodiment, in comparison between the semiconductor strain sensor module of the first embodiment shown in FIG. 5 and the semiconductor strain sensor module of PTL 1 shown in FIG. 8.

The effect of the present embodiment will be described based on the comparison between the semiconductor strain sensor module of the present embodiment and the semiconductor strain sensor module of PTL 1, using FIGS. 8 to 10. First, a structure in which the semiconductor strain sensor module of PTL 1 is fastened to the object to be measured will be described using FIG. 8. FIG. 8 is a perspective view showing the structure.

As shown in FIG. 8, the structure in which the semiconductor strain sensor module of PTL 1 is fastened to the object to be measured employs a structure for fixing both sides of the semiconductor strain sensor module to the object 110 to be measured with screws 111. In FIG. 8, the semiconductor strain sensor 106 is connected to the metal body 107, the metal body 107 has two left and right portions on both longitudinal sides of the semiconductor strain sensor 106, and the left and right portions are connected to the object 110 to be measured with the screws 111.

Next, the effect of semiconductor strain sensor module of the present embodiment will be described, while comparing the semiconductor strain sensor module of the present embodiment with the semiconductor strain sensor module of PTL 1 shown in FIG. 8, using FIGS. 9(a) and 9(b). FIGS. 9(a) and 9(b) show an example of the effect. FIGS. 9(a) and 9(b) show thermal expansion of the objects 10, 110 to be measured with rising temperature, wherein FIG. 9(a) corresponds to PTL 1, and FIG. 9(b) corresponds to the present embodiment.

In FIGS. 9(a) and 9(b), it is assumed that, for simplification of the description, the initial lengths L of the metal bodies 7 and 107 and the objects 10, 110 to be measured are uniformized, a joining point between the metal body 7 and the object 10 to be measured, at an initial temperature T1, is shown only at a left end (screw 11) in the present embodiment, and joining points between the metal body 107 and the object 110 to be measured, at the initial temperature T1, are shown at both ends (screws 111) in an example of PTL 1, and frictional influences between the metal bodies 7, 107 and the objects 10, 110 to be measured are eliminated except at the fastened portions.

The thermal expansion of the metal bodies 7 and 107 and the objects 10, 110 to be measured are shown, wherein a temperature T2 is higher than the initial temperature T1 by $\Delta T$. Quantities $\Delta L1$, $\Delta L2$ representing the longitudinal change in expansion between the metal bodies 7, 107 and the objects 10, 110 to be measured are expressed by the following formulas, wherein the thermal expansion coefficients of the metal bodies 7, 107 are denoted by $\alpha 1$, the thermal expansion coefficients of the objects 10, 110 to be measured are denoted by $\alpha 2$, and the temperature rise is denoted by $\Delta T$.

$$\Delta L1 = L\alpha 1 \Delta T$$

$$\Delta L2 = L\alpha 2 \Delta T$$

In the example of PTL 1 shown in FIG. 9(a), the metal body 107 and the object 110 to be measured are fastened on both sides with the screws 111, so that the metal body is changed to have the quantity $\Delta L2$ equal to the thermal expansion of the object 110 to be measured. In this case, the metal body 107 is unnecessarily expanded by a quantity expressed by $\Delta L2 - \Delta L1$ relative to the quantity $\Delta L1$ representing the original expansion of the metal body. Accordingly, the metal body 107 is not expanded isotropically as shown in FIG. 4, the influence of the thermal strain is not canceled in the bridge circuit in the semiconductor strain sensor 106, and the thermal strain affects an output voltage from the semiconductor strain sensor 106.

On the other hand, the present embodiment shown in FIG. 9(b) provides the structure in which only one sides of the metal body and the object to be measured are fastened with the screw 11. Therefore, the influence of the thermal expansion of the object 10 to be measured is negligible in thermal expansion of the metal body 7 (original quantity $\Delta L1$ of the expansion of the metal body 7), and the isotropy is maintained as shown in FIG. 4 to cancel the influence of the thermal strain in the bridge circuit in the semiconductor strain sensor 6.

Figure 10:
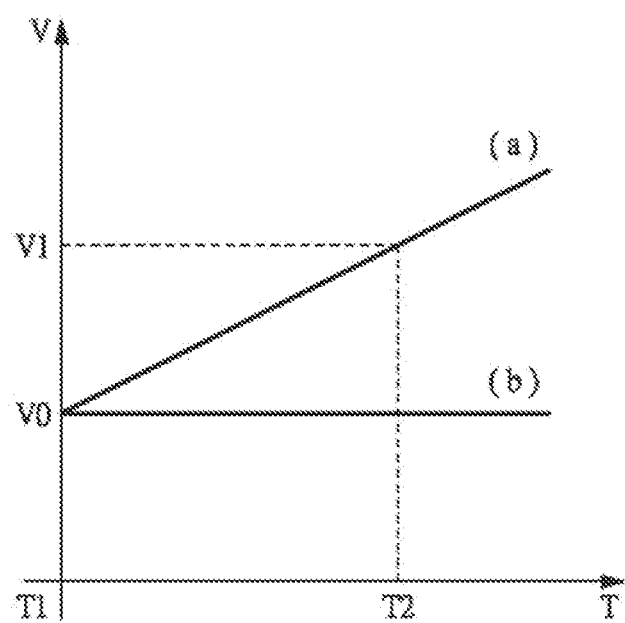
FIG. 10 shows an example of the variation of output voltages of the semiconductor strain sensor during thermal expansion in comparison between the semiconductor strain sensor module of the first embodiment shown in FIG. 5 and the semiconductor strain sensor module of PTL 1 shown in FIG. 8.
Figure 11:
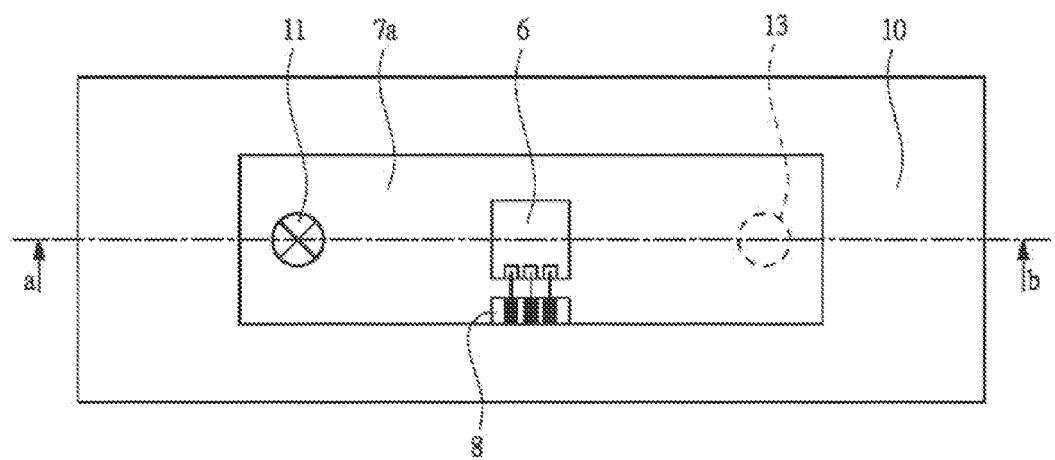
FIGS. 11(a) and 11(b) are a plan view and a cross-sectional view, respectively, showing an example of a structure in which a semiconductor strain sensor module (metal body with a projection) as a second embodiment of the device for measuring mechanical quantity of the present invention is fastened to the object to be measured.
Figure 11:
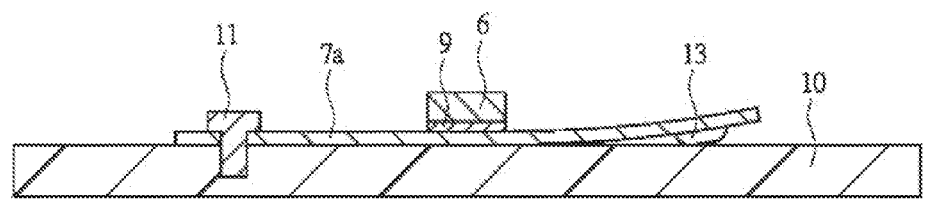
Figure 12:
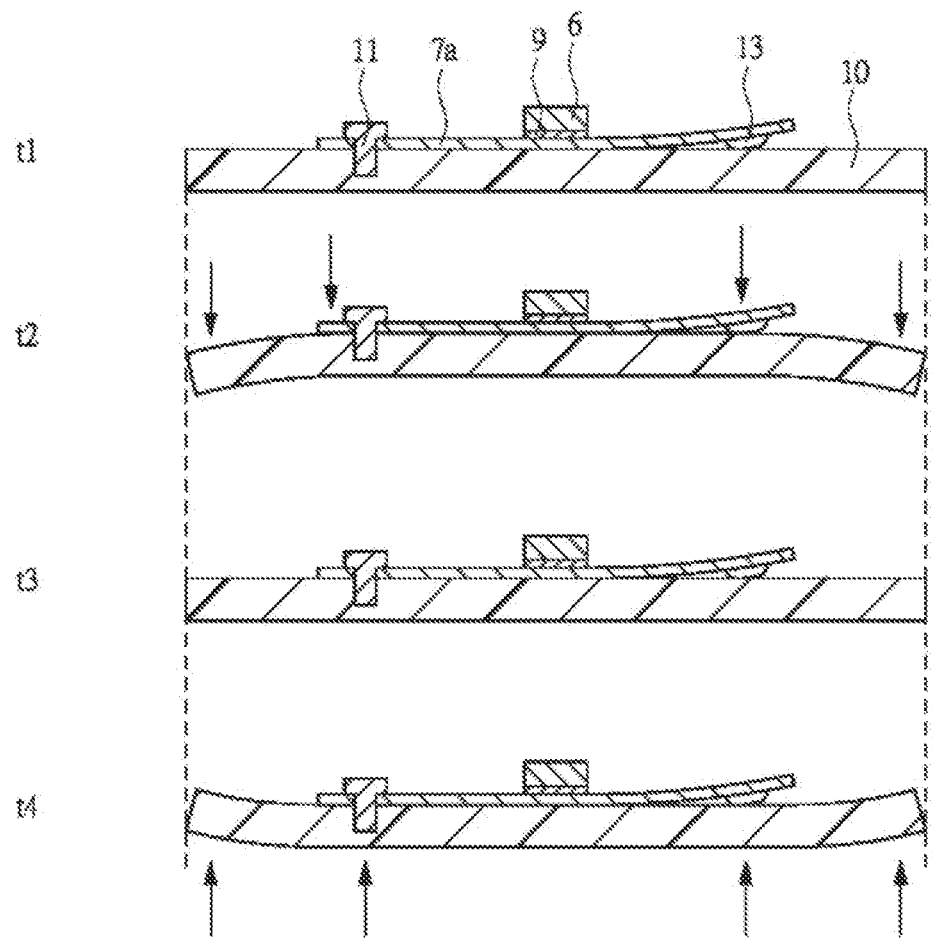
FIGS. 12(a) and 12(b) show an example of the operations of the structure shown in FIG. 11 in which the semiconductor strain sensor module is fastened to the object to be measured and output voltages of the semiconductor strain sensor.
Figure 12:
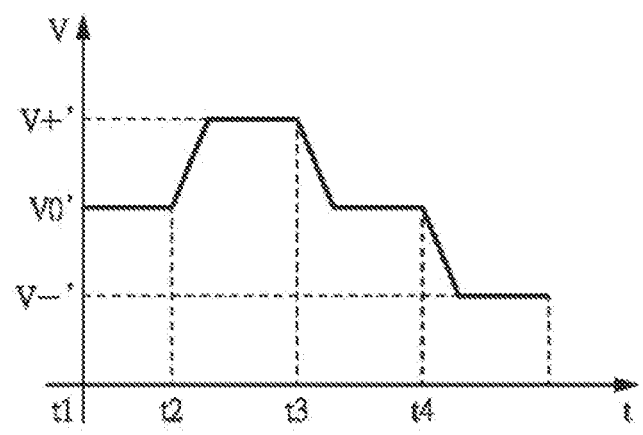

Variation of output voltages of the semiconductor strain sensors 6, 106 of the example of PTL 1 and the present embodiment, at the temperatures T1, T2, are shown in FIG. 10. FIG. 10 shows an example of variation of output voltages of the semiconductor strain sensors 6, 106 during the thermal expansion.

The example of PTL 1 expresses an output voltage varying with the temperature rise due to the thermal strain, as shown as a variation property (a), but the example of the present embodiment expresses a constant output voltage with reduced influence of the thermal strain with the temperature rise, as shown as a variation property (b). In this manner, the present embodiment can reduce the influence of the thermal strain, even when the object 10 to be measured has a thermal expansion coefficient larger than that of the metal body 7 by approximately one digit.

As described above, the semiconductor strain sensor module of the present embodiment includes the metal body 7 and the semiconductor strain sensor 6, the object 10 to be measured is made of the material having a thermal expansion coefficient larger than that of the metal body 7, and the metal body 7 on which the semiconductor strain sensor 6 is mounted is fixed to the object 10 to be measured. Especially, only one side of the metal body 7 is fixed to the object 10 to be measured. Such a structure provides the following effects.

Even when the metal body 7 on which the semiconductor strain sensor 6 is mounted is fixed to the object 10 to be measured, such as the plastic resin, having a thermal expansion coefficient different by approximately one digit from that of the metal body 7, the influence of the thermal strain caused by the difference in thermal expansion coefficient is reduced to facilitate detection of the mechanical quantity, such as the deformation quantity or strain quantity, of the object 10 to be measured generated upon application of the force to the object 10 to be measured, and the mechanical quantity can be precisely measured.

In other words, when the thermal expansion is generated in the object 10 to be measured as the temperature changes, the isotropy is not lost in the thermal expansion of the metal body 7 on which the semiconductor strain sensor 6 is mounted, the influence of the thermal strain can be canceled in the bridge circuit mounted in the semiconductor strain sensor 6, and deterioration in measurement precision can be reduced which is caused by the temperature change.

Thus, the semiconductor strain sensor module is achieved which reduces the influence of the difference in thermal expansion coefficient between the object 10 to be measured and the base plate metal body 7, and enables the precise measurement of the mechanical quantity, such as the deformation quantity or strain quantity, caused in the object 10 to be measured.

[Second Embodiment]

A semiconductor strain sensor module a second embodiment of the device for measuring mechanical quantity of the present invention will be described using FIGS. 11(a) to 12(b). The present embodiment is different from the first embodiment in that a metal body has a projection on a surface making contact with an object to be measured. The present embodiment will be described mainly in view of difference from the first embodiment.

The semiconductor strain sensor module according to the present embodiment will be described using FIGS. 11(a) and 11(b). FIG. 11(a) is a plan view and FIG. 11(b) is a cross-sectional view (cross-sectional view taken along cut line a-b of FIG. 11(a)) which show an example of a structure in which the semiconductor strain sensor module (metal body 7a having projection 13) is fastened to the object 10 to be measured. As shown in FIGS. 11(a) and 11(b), the semiconductor strain sensor module of the present embodiment includes the projection 13 provided on one side of the metal body 7a (opposite to a side fastened with the screw 11), specifically on a surface of the metal body 7a making contact with the object 10 to be measured.

The effects of the present embodiment having such a structure will be described using FIGS. 12(a) and 12(b). FIG. 12(a) shows an example of operations of the structure in which the semiconductor strain sensor module is fastened to the object 10 to be measured, and FIG. 12(b) shows output voltages of the semiconductor strain sensor 6.

As shown in FIGS. 12(a) and 12(b), according to the present embodiment, a negative pressure is applied to the metal body 7a through the projection 13 at a time t1 at which the object 10 to be measured is not deformed, and "compression strain" has already been generated (output voltage V0' of semiconductor strain sensor 6) on a surface of the metal body 7a. When a certain downward load is applied to both ends of the metal body 7a from the initial condition to a time t2, the "compression strain" generated on the surface of the metal body 7a is reduced. A time required before reduction of the "compression strain" is started is shorter than a delay time in which the "bending strain" is generated on the surface of the metal body 7 with respect to a load applied from the time t2 in the first embodiment, and a response time of the object 10 to be measured, expanding from the initial condition to a time at which the voltage rises to V+' through a transient condition, is effectively reduced.

Similarly, when the metal body 7a is restored to the initial condition before the time t3 and a certain upward load is applied to both ends of the metal body after the time t4, a time required to lower output voltage of the semiconductor strain sensor 6 to V−' through the transient condition is shorter than a delay time required to generate "compression strain" on the surface of the metal body 7 after the application of the upward load from the initial condition after the time t4 in the first embodiment, and the response time is effectively reduced with respect to the variation of the object 10 to be measured from the initial condition.

As described above, according to the semiconductor strain sensor module of the present embodiment, the metal body 7a has the projection 13 on a surface making contact with the object 10 to be measured, and thus the response time to the variation of the object 10 to be measured from the initial condition can be reduced as an effect different from the first embodiment.

In the present embodiment, the projection 13 is formed on the surface of the metal body 7a making contact with the object 10 to be measured, but it is possible to employ any structure for generating a negative pressure on the metal body on which the semiconductor strain sensor is connected, in the initial condition in which any load is not applied to the object to be measured.

[Third Embodiment]

Figure 13:
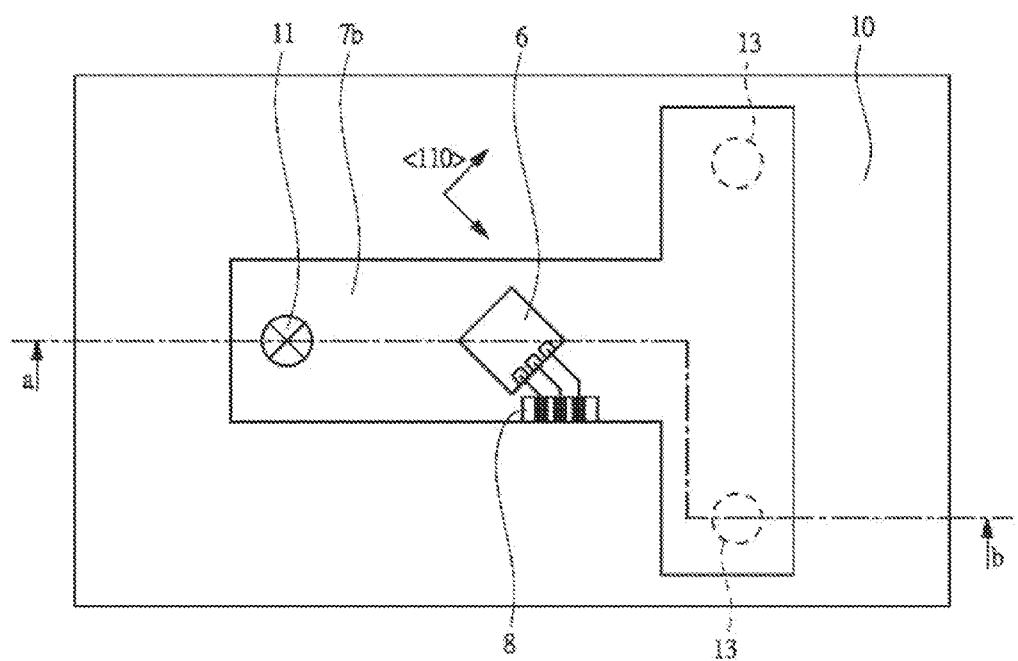
FIGS. 13(a) and 13(b) are a plan view and a cross-sectional view, respectively, showing an example of a structure in which a semiconductor strain sensor module (T-shaped metal body) as a third embodiment of the device for measuring mechanical quantity of the present invention is fastened to the object to be measured.
Figure 13:
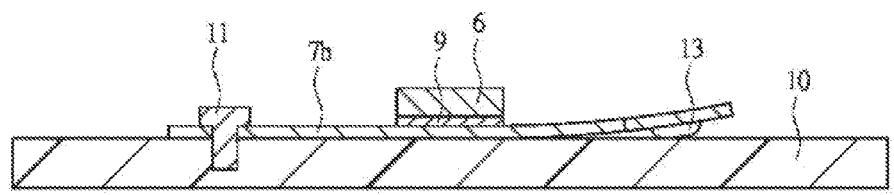

A semiconductor strain sensor module as a third embodiment of the device for measuring mechanical quantity of the present invention will be described using FIGS. 13(a) and 13(b). The present embodiment is different from the first and second embodiments in that a metal body is formed into a T-shape. The present embodiment will be described mainly in view of difference from the first and second embodiments.

The semiconductor strain sensor module according to the present embodiment will be described using FIGS. 13(a) and 13(b). In FIG. 13(a) is a plan view and FIG. 13(b) is a cross-sectional view (cross-sectional view taken along a cut line a-b of FIG. 13(a)) which show an example of a structure in which the semiconductor strain sensor module (T-shaped metal body 7b) is fastened to an object 10 to be measured. As shown in FIGS. 13(a) and 13(b), in the semiconductor strain sensor module of the present embodiment, the metal body 7b has a T-shape, a semiconductor strain sensor 6 is turned by 45 degrees to be bonded to substantially the center of the metal body 7b, and a silicon <110> orientation is directed in a shearing direction. In the T-shaped metal body 7b, projections 13 are formed on both (two) sides of a horizontal arm of a T-shape, and a lower side of a vertical arm is fixed with a screw 11. The semiconductor strain sensor 6 is connected at substantially the center part of the vertical arm of the T-shape by being turned by 45 degrees relative to a longitudinal direction.

The present embodiment having such a structure effectively generates shearing strain at the center part of the metal body 7b due to the T-shape of the metal body 7b, when the T shape causes torsion in the object 10 to be measured, and the torsion of the object 10 to be measured is readily detected.

As described above, according to the semiconductor strain sensor module of the present embodiment, the T-shaped metal body 7b facilitates the detection of the torsion of the object 10 to be measured as an effect different from those of the first and second embodiments.

[Fourth Embodiment]

Figure 14:
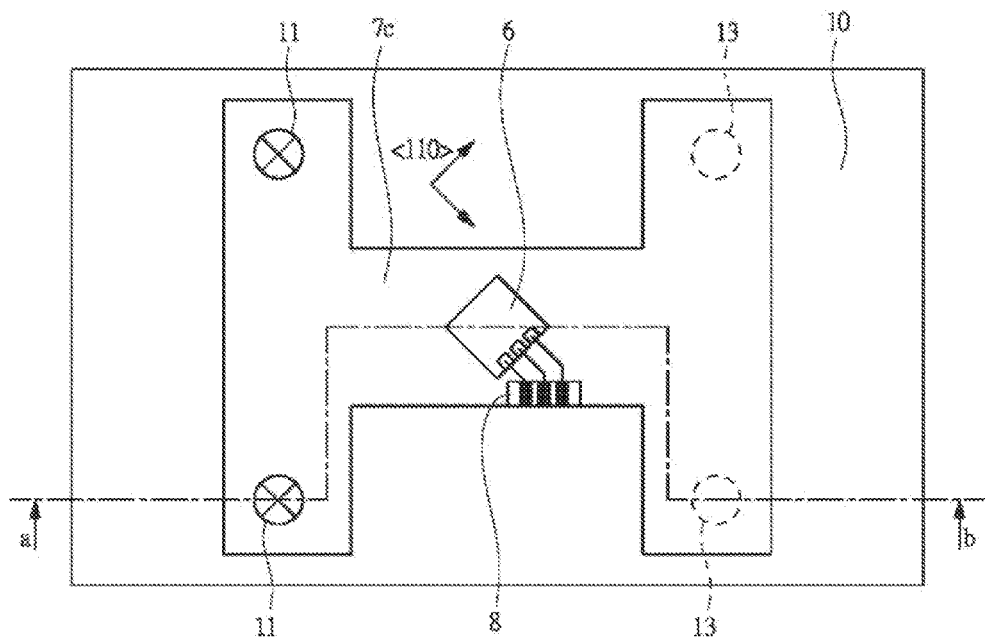
FIGS. 14(a) and 14(b) are a plan view and a cross-sectional view, respectively, showing an example of a structure in which the semiconductor strain sensor module (H-shaped metal body) as a fourth embodiment of the device for measuring mechanical quantity of the present invention is fastened to the object to be measured.
Figure 14:
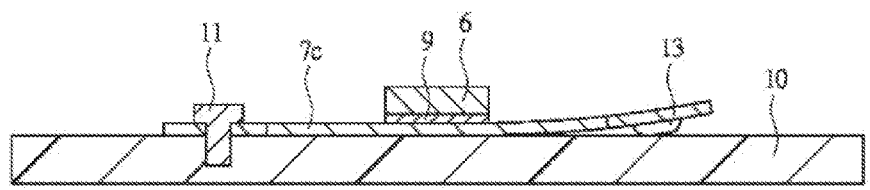

A semiconductor strain sensor module as a fourth embodiment of the device for measuring mechanical quantity of the present invention will be described in detail using FIGS. 14(a) and 14(b). The present embodiment is different from the above-mentioned first to third embodiments, particularly from the third embodiment, in that a metal body is formed into an H-shape. The present embodiment will be mainly described mainly in view of difference from the above-mentioned third embodiment.

The semiconductor strain sensor module according to the present embodiment will be described using FIGS. 14(a) and 14(b). FIG. 14(a) is a plan view and FIG. 14(b) is a cross-sectional view (taken along a cut line a-b of FIG. 14(a)) which show an example of a structure in which the semiconductor strain sensor module (H-shaped metal body 7c) is fastened to an object 10 to be measured. As shown in FIGS. 14(a) and 14(b), the semiconductor strain sensor module of the present embodiment includes the metal body 7c formed into an H-shape, and the metal body 7c is further fixed with two screws 11. The H-shaped metal body 7c has a right-side vertical arm and a left-side vertical arm of the H-shape, and projections 13 are formed on both (two) sides of the right-side vertical arm, and both (two) sides of the left-side vertical arm are fixed with the screws 11. The semiconductor strain sensor 6 is turned by 45 degrees to be bonded to substantially the center of a horizontal arm of the H-shape.

The present embodiment having such a structure further effectively generates shearing strain at the center of the metal body 7c as compared with the third embodiment due to the H-shaped metal body 7c, when the H shape generates torsion in the object 10 to be measured, and the torsion of the object 10 to be measured is more readily detected.

As described above, according to the semiconductor strain sensor module of the present embodiment, the metal body 7c formed into the H-shape further facilitates the detection of torsion of the object 10 to be measured as an effect different from that of the third embodiment.

[Fifth Embodiment]

A semiconductor strain sensor module as a fifth embodiment of the device for measuring mechanical quantity of the present invention will be described in detail using FIG. 15.

The present embodiment is different from the first to fourth embodiments in that the metal body has a pipe shape, a first semiconductor strain sensor is mounted on the upper surface of the metal body, and a second semiconductor strain sensor is mounted on a lateral side of the metal body. The present embodiment will be mainly described in view of difference from the above-mentioned first to fourth embodiments.

The semiconductor strain sensor module according to the present embodiment will be described using FIG. 15.

Figure 15:
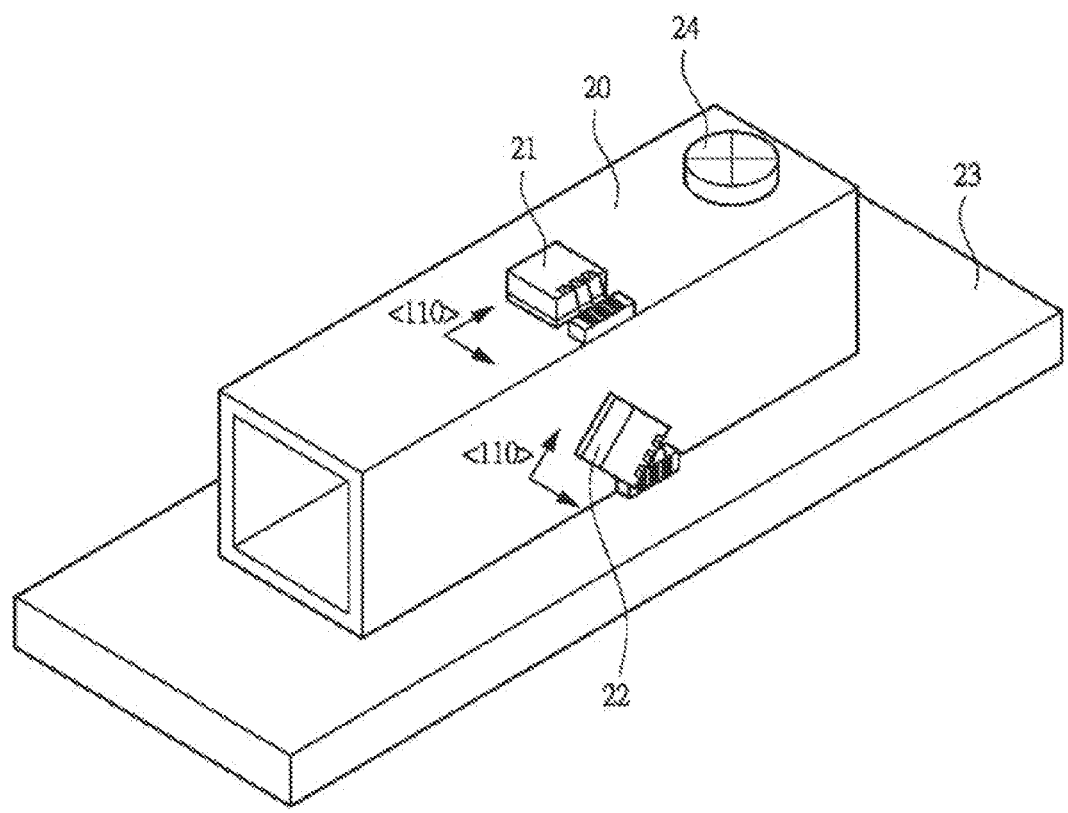
FIG. 15 is a perspective view showing an example of a structure in which a semiconductor strain sensor module (pipe-shaped metal body) as a fifth embodiment of the device for measuring mechanical quantity of the present invention is fastened to the object to be measured.

FIG. 15 is a perspective view showing an example of a structure in which the semiconductor strain sensor module (pipe-shaped metal body 20) is fastened to an object 23 to be measured. As shown in FIG. 15, the semiconductor strain sensor module of the present embodiment includes the metal body 20 having a shape of square pipe, a semiconductor strain sensor 21 connected such that the longitudinal direction of the upper surface of the metal body 20 is directed in the silicon <110> orientation, and a semiconductor strain sensor 22 connected such that the shearing direction of a side surface of the metal body 20 is directed in the silicon <110> orientation. One side of the metal body 20 is fastened to the object 23 to be measured with a screw 24 as a fastener.

The effect of the present embodiment provided by such a structure is that the semiconductor strain sensor 21 connected to the upper surface of the pipe-shaped metal body 20 detects "bending strain" and "compression strain" caused on the upper surface of the metal body 20 by a load on the object 23 to be measured, and the semiconductor strain sensor 22 connected to a side surface of the pipe-shaped metal body 20 detects "shearing strain" caused on the side surface of the metal body 20 upon generation of torsion in the object 23 to be measured.

As described above, in the semiconductor strain sensor module of the present embodiment, the metal body 20 has a pipe shape, the first semiconductor strain sensor 21 is mounted on the upper surface of the metal body 20, and the second semiconductor strain sensor 22 is mounted on the side surface of the metal body 20. With this configuration, the semiconductor strain sensor module of the present embodiment can detect the "bending strain" and "compression strain" caused on the upper surface of the metal body 20, and detect "shearing strain" caused on the side surface of the metal body 20 upon generation of the torsion in the object 23 to be measured, as effects different from those of the first to fourth embodiments.

[sixth Embodiment]

Figure 16:
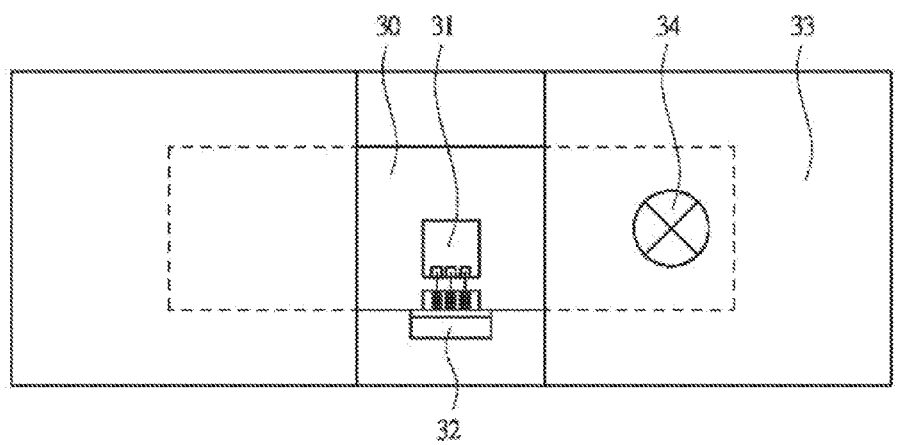
FIGS. 16(a) and 16(b) are a plan view and a cross-sectional view, respectively, showing an example of a structure in which a semiconductor strain sensor module (metal body making contact with the object to be measured on both surfaces) as a sixth embodiment of the device for measuring mechanical quantity of the present invention is fastened to the object to be measured.
Figure 16:
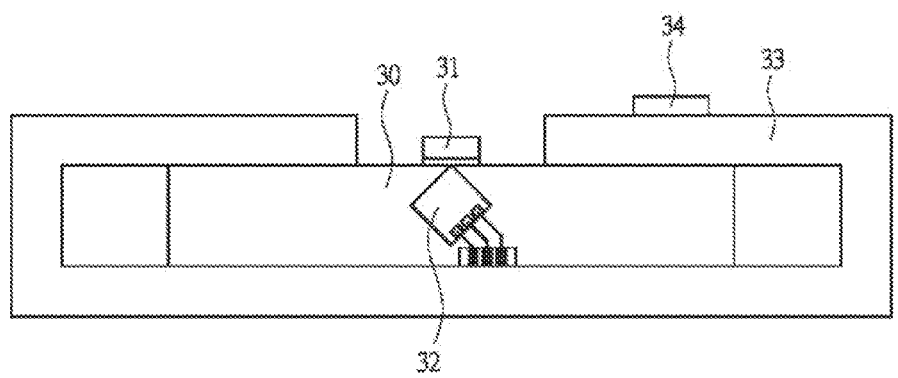

A semiconductor strain sensor module as a sixth embodiment of the device for measuring mechanical quantity of the present invention will be described in detail using FIGS. 16(a) and 16(b). The present embodiment is different from the first to fifth embodiments in that a metal body has front and back surfaces making contact with an object to be measured. The present embodiment will be mainly described in view of difference from the above-mentioned first to fifth embodiments.

The semiconductor strain sensor module according to the present embodiment will be described using FIGS. 16(a) and 16(b). FIG. 16(a) is a plan view and FIG. 16(b) is a side view which show an example of a structure in which the semiconductor strain sensor module (metal body 30 making contact with an object 33 to be measured on the front and back surfaces) is fastened to the object 33 to be measured. As shown in FIGS. 16(a) and 16(b), in the semiconductor strain sensor module of the present embodiment, the object 33 to be measured makes contact with both of front and back surfaces of the metal body 30. The metal body 30 is formed into a square pipe shape, a semiconductor strain sensor 31 is connected such that a longitudinal direction of the upper surface of the metal body 30 is directed in the silicon <110> orientation, and a semiconductor strain sensor 32 is connected such that a shearing direction of a side surface of the metal body 30 is directed in the silicon <110> orientation. Further, the object 33 to be measured is fastened on one side of the metal body 30 with a screw 34 as a fastener.

As described in the present embodiment, the object 33 to be measured has contact points on the front and back surfaces of the metal body 30 on which the semiconductor strain sensors 31 and 32 are mounted. Therefore, deformation quantity or strain quantity of the object 33 to be measured is transmitted to the semiconductor strain sensors 31 and 32 on the metal body 30 through the front and back surfaces of the metal body 30. Accordingly, the semiconductor strain sensors 31 and 32 on the metal body 30 allow precise measurement of the deformation quantity or strain quantity.

As described above, according to the semiconductor strain sensor module of the present embodiment, the object 33 to be measured makes contact with the front and back surfaces of the metal body 30, so that the deformation quantity or strain quantity of the object 33 to be measured, transmitted through the front and back surfaces of the metal body 30, can be precisely measured, as an effect different from those of the first to fifth embodiments.

In the present embodiment, the metal body 30 having a square pipe shape has been described as an example, but a structure in which a metal body has a plate shape, a semiconductor strain sensor is connected on the upper surface of the plate-shaped metal body, and an object to be measured makes contact with the front and back surfaces of the metal body may be also employed.

[Seventh Embodiment]

Figure 17:
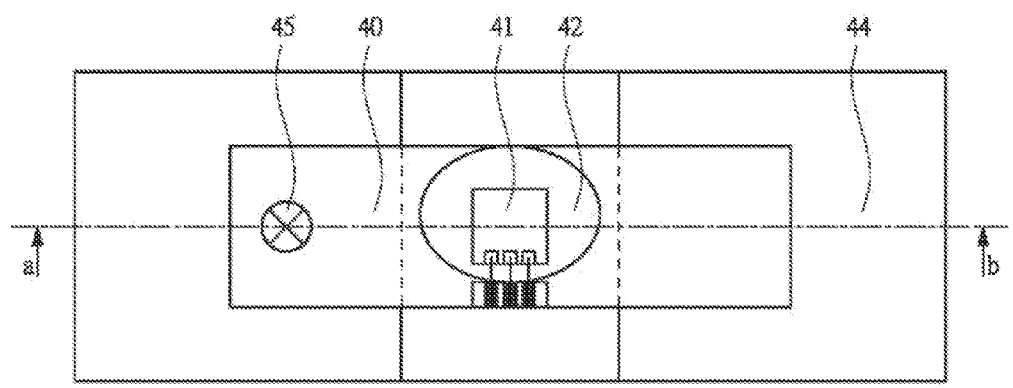
FIGS. 17(a) and 17(b) are a plan view and a cross-sectional view, respectively, showing an example of a structure in which a semiconductor strain sensor module (metal body having a molded resin on the upper and back surfaces) as a seventh embodiment of the device for measuring mechanical quantity of the present invention is fastened to the object to be measured.
Figure 17:
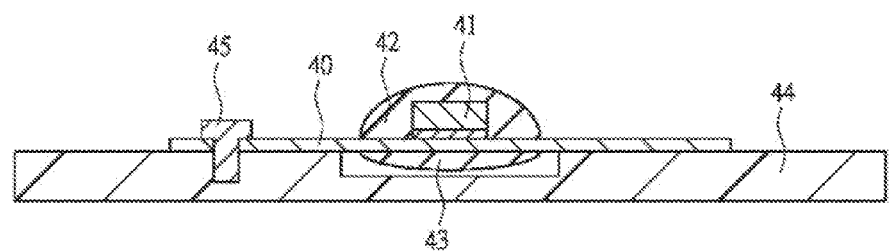

A semiconductor strain sensor module as a seventh embodiment of the device for measuring mechanical quantity of the present invention will be described in detail using FIGS. 17(a) and 17(b). The present embodiment is different from the first to sixth embodiments in that the semiconductor strain sensor module has a first molded resin for covering a semiconductor strain sensor mounted on a metal body, and a second molded resin for covering the back surface of the metal body on which the semiconductor strain sensor is mounted, to be symmetrical to the first molded resin. The present embodiment will be mainly described in view of difference from the above-mentioned first to sixth embodiments.

The semiconductor strain sensor module according to the present embodiment will be described using FIGS. 17(a) and 17(b). FIG. 17(a) is a plan view and FIG. 17(b) is a cross-sectional view (cross-sectional view taken along a cut line a-b of FIG. 17(a)) which show an example of a structure in which the semiconductor strain sensor module (the metal body 40 having the molded resins 42 and 43 on the front and back surfaces) is fastened to an object 44 to be measured. As shown in FIGS. 17(a) and 17(b), the semiconductor strain sensor module of the present embodiment has the molded resin 42 on the semiconductor strain sensor 41 connected to the metal body 40, and the molded resin 43 disposed on the back side of the metal body 40 and at a position symmetrical to the molded resin 42. The metal body 40 is formed into a plate shape, and the semiconductor strain sensor 41 is connected longitudinally on the upper surface of the metal body 40 to be directed in the silicon <110> orientation. Further, the object 44 to be measured is fastened on one side of the metal body 40 with a screw 45 as a fastener.

Usually, when the molded resin 42 is attached on the upper surface of the semiconductor strain sensor 41, the entire metal body 40 is pulled by the molded resin 42 due to a difference in thermal expansion coefficient with the change in temperature, and subjected to thermal strain. Therefore, in the present embodiment, the molded resin 43 is attached also on the back surface of the metal body 40 to be symmetrical to the upper surface of the semiconductor strain sensor 41, so that the upper and back surfaces of the metal body 40 are pulled, and the effect of the thermal strain is effectively reduced.

As described above, the semiconductor strain sensor module of the present embodiment has the first molded resin 42 for covering the semiconductor strain sensor 41 mounted on the metal body 40, and the second molded resin 43 for covering the back surface of the metal body 40 on which the semiconductor strain sensor 41 is mounted, to be symmetrical to the first molded resin 42. Therefore, the influence of the thermal strain can be reduced when covering the upper surface of the semiconductor strain sensor 41 with the molded resin 42, as an effect different from those of the first to sixth embodiments.

In the present embodiment, the metal body 40 having a plate shape has been described as an example, but a structure in which a metal body has a pipe shape, a surface of the pipe-shaped metal body mounted with the semiconductor strain sensor, and the back surface thereof are covered with the molded resin, is also employed.

The invention made by the inventors has been described in detail based on the embodiments, but it goes without saying that the invention is not limited to the embodiments, and the invention may be modified without departing from the spirit thereof.

INDUSTRIAL APPLICABILITY

The device for measuring mechanical quantity of the present invention is applicable to especially a device for measuring mechanical quantity, such as deformation quantity or strain quantity, generated in an object to be measured, such as a resin, having a large thermal expansion coefficient.

REFERENCE SIGNS LIST 1 (R1, R2, R3, R4) p-type diffused resistor
2 power terminal
3 ground terminal
4 amplifier
5 output terminal
6 semiconductor strain sensor
7, 7a, 7b, 7c metal body
8 terminal base
9 connection material
10 object to be measured
11 screw
13 projection metal body
21 semiconductor strain sensor
22 semiconductor strain sensor
23 object to be measured
24 screw
30 metal body
31 semiconductor strain sensor
32 semiconductor strain sensor
33 object to be measured
34 screw
40 metal body
41 semiconductor strain sensor
42 molded resin
43 molded resin
44 object to be measured
45 screw
106 semiconductor strain sensor
107 metal body
110 object to be measured
111 screw

The invention claimed is:

1. A device for measuring mechanical quantity, the device measuring deformation quantity of an object to be measured, the device comprising:
   a metal body; and
   a semiconductor strain sensor mounted on the metal body and configured to detect strain of the metal body;
   wherein the object to be measured includes a material having a thermal expansion coefficient larger than that of the metal body, the metal body mounted with the semiconductor strain sensor has a structure to be fixed to the object to be measured, and the object to be measured is fixed only on one side of the metal body mounted with the semiconductor strain sensor; and
   wherein the metal body comprises a projection on a surface making contact with the object to be measured, and the metal body generates "compression strain" by a negative pressure through the projection, while no load is applied to the object to be measured.

2. A device for measuring mechanical quantity, the device measuring deformation quantity of an object to be measured, the device comprising:
   a metal body; and
   a semiconductor strain sensor mounted on the metal body and configured to detect strain of the metal body;
   wherein the object to be measured includes a material having a thermal expansion coefficient larger than that of the metal body, the metal body mounted with the semiconductor strain sensor has a structure to be fixed to the object to be measured, and the object to be measured is fixed only on one side of the metal body mounted with the semiconductor strain sensor;
   wherein the semiconductor strain sensor comprises a sensor configured to detect "shearing strain;" and
   wherein the semiconductor strain sensor is connected to the metal body by being turned by 45 degrees relative to a longitudinal direction of the metal body, and a silicon <110> orientation is directed in a shearing direction.

3. A device for measuring mechanical quantity, the device measuring deformation quantity of an object to be measured, the device comprising:
   a metal body having a pipe shape;
   a first semiconductor strain sensor mounted on an upper surface of the metal body and configured to detect strain of the metal body; and
   a second semiconductor strain sensor mounted on a side surface of the metal body and configured to detect strain of the metal body,
   wherein the object to be measured includes a material having a thermal expansion coefficient larger than that of the metal body,
   the metal body mounted with the first semiconductor strain sensor and the second semiconductor strain sensor has a structure to be fixed to the object to be measured, and
   the object to be measured is fixed only on one side of the metal body mounted with the first semiconductor strain sensor and the second semiconductor strain sensor.

4. The device for measuring mechanical quantity according to claim 3, wherein the first semiconductor strain sensor comprises a sensor configured to detect "bending strain" and "compression strain", and the second semiconductor strain sensor comprises a sensor configured to detect "shearing strain".

5. The device for measuring mechanical quantity according to claim 4, wherein the first semiconductor strain sensor is connected to the metal body such that a longitudinal direction of an upper surface of the metal body is directed in a silicon <110>orientation, and the second semiconductor strain sensor is connected to the metal body such that a shearing direction of a side surface of the metal body is directed in the silicon <110>orientation.

6. A device for measuring mechanical quantity, the device measuring deformation quantity of an object to be measured, the device comprising:

a metal body; and a semiconductor strain sensor mounted on the metal body and configured to detect strain of the metal body;

wherein the object to be measured includes a material having a thermal expansion coefficient larger than that of the metal body, the metal body mounted with the semiconductor strain sensor has a structure to be fixed to the object to be measured, and the object to be measured is fixed only on one side of the metal body mounted with the semiconductor strain sensor; and wherein the object to be measured is fixed to the metal body such that the object to be measured makes contact with the front and back surfaces of the metal body.

7. A device for measuring mechanical quantity of an object to be measured, the device measuring deformation quantity of an object to be measured, the device comprising:

a metal body;

a semiconductor strain sensor mounted on the metal body and configured to detect strain of the metal body;

a first molded resin for covering the semiconductor strain sensor mounted on the metal body; and a second molded resin for covering the back surface of the metal body mounted with the semiconductor strain sensor so as to be symmetrical to the first molded resin;

wherein the object to be measured includes a material having a thermal expansion coefficient larger than that of the metal body, the metal body mounted with the semiconductor strain sensor has a structure to be fixed to the object to be measured, and the object to be measured is fixed only on one side of the metal body mounted with the semiconductor strain sensor.

* * * * *